United States Patent [19]

Lim et al.

[11] 4,389,419
[45] Jun. 21, 1983

[54] VITAMIN ENCAPSULATION

[75] Inventors: Franklin Lim, Richmond; Richard D. Moss, Chester, both of Va.

[73] Assignee: Damon Corporation, Needham Heights, Mass.

[21] Appl. No.: 205,340

[22] Filed: Nov. 10, 1980

[51] Int. Cl.³ .................. A23L 1/30; B01J 13/02
[52] U.S. Cl. ........................ 426/72; 426/73; 426/575; 427/213.3; 264/4.1
[58] Field of Search .............. 252/316; 424/35, 22; 426/72, 73, 575

[56] References Cited

U.S. PATENT DOCUMENTS

| | | |
|---|---|---|
| 1,879,762 | 9/1932 | Nitardy. |
| 1,964,867 | 7/1934 | Allyn ............................ 99/11 |
| 2,022,464 | 11/1935 | Hall .............................. 167/81 |
| 2,183,053 | 12/1939 | Taylor ........................... 99/11 |
| 2,218,591 | 10/1940 | Taylor ........................... 99/11 |
| 2,348,503 | 5/1944 | Taylor .......................... 167/81 |
| 2,375,279 | 5/1945 | Buxton et al. ................. 99/11 |
| 2,410,417 | 11/1946 | Andersen ...................... 167/81 |
| 2,643,209 | 6/1953 | Goett et al. ................... 167/81 |
| 2,650,895 | 9/1953 | Wallenmeyer et al. ........ 167/81 |
| 2,691,619 | 10/1954 | Bavley et al. ................. 167/81 |
| 2,756,177 | 7/1956 | Cannalonga et al. .......... 167/81 |
| 2,827,452 | 3/1958 | Schlenk et al. ................ 260/209 |
| 2,828,206 | 3/1958 | Rosenberg ..................... 99/2 |
| 2,897,119 | 7/1959 | Dunn ............................ 167/81 |
| 2,940,900 | 6/1960 | Benton et al. ................. 167/81 |
| 2,987,444 | 6/1961 | Allardice ....................... 167/81 |
| 3,028,308 | 4/1962 | Zambito et al. ............... 167/82 |
| 3,056,728 | 10/1962 | Ohtaki ........................... 167/81 |
| 3,099,602 | 7/1963 | Anderson ...................... 167/81 |
| 3,137,630 | 6/1964 | Hecker et al. ................. 167/81 |
| 3,143,475 | 8/1964 | Koff et al. ..................... 167/81 |
| 3,159,585 | 12/1964 | Evans et al. ................... 252/316 |
| 3,173,838 | 3/1965 | Brooks .......................... 167/81 |
| 3,202,731 | 8/1965 | Grevenstuk et al. ........... 264/7 |
| 3,293,132 | 12/1966 | Stoyle, Jr. et al. ............. 167/82 |
| 3,361,632 | 1/1968 | Ross et al. ..................... 167/83 |
| 3,445,563 | 5/1969 | Clegg et al. ................... 424/35 |
| 3,574,826 | 4/1971 | Shepherd ...................... 424/81 |
| 3,608,083 | 9/1971 | Bunnell et al. ................ 424/284 |
| 3,666,678 | 5/1972 | Mosler et al. ................. 252/316 |
| 3,733,205 | 5/1973 | Shovers et al. ................ 99/48 |
| 3,749,799 | 7/1973 | Cort et al. ..................... 424/344 |
| 3,819,838 | 6/1974 | Smith et al. ................... 426/89 |
| 3,860,733 | 1/1975 | Morse et al. .................. 426/302 |
| 3,869,539 | 3/1975 | Kring et al. ................... 424/236 |
| 3,914,430 | 10/1975 | Cannalonga et al. .......... 424/284 |
| 3,962,416 | 6/1976 | Katzen .......................... 424/19 |
| 3,971,852 | 7/1976 | Brenner et al. ................ 426/103 |
| 4,020,005 | 4/1977 | Lang ............................. 252/316 |
| 4,254,100 | 3/1981 | Keller et al. ................... 424/35 X |

FOREIGN PATENT DOCUMENTS

| | | | |
|---|---|---|---|
| 762700 | 12/1956 | United Kingdom | 264/4 |
| 931148 | 7/1963 | United Kingdom | 252/316 |
| 1310715 | 3/1973 | United Kingdom | 252/316 |

*Primary Examiner*—Richard D. Lovering
*Attorney, Agent, or Firm*—Lahive & Cockfield

[57] ABSTRACT

Disclosed is a process for encapsulating oils and oil-soluble substances in multi-compartmentalized, mechanically stable microcapsules. The process comprises the steps of first forming an emulsion consisting of a continuous phase comprising an aqueous solution of an alkali metal alginate and optionally a water-soluble, alcohol-insoluble filler such as a polysaccharide, and a dispersed phase of an oleophilic substance such as one or more vitamins dissolved in an oil. The emulsion is then formed into droplets which are thereafter immersed in an alcoholic solution of multivalent cations, to produce a shape-retaining alginate matrix filled with precipitated polysaccharide and enclosing plural oil droplets. The vitamins are thereby protected from oxidative degradation and can be handled like conventional crystalline solids.

21 Claims, No Drawings

VITAMIN ENCAPSULATION

BACKGROUND OF THE INVENTION

This invention relates to a method of encapsulating oils and oil-soluble materials, such as vitamins A, D, and E, which dispenses with the use of gelatins. More particularly, it relates to a method of producing ingestible microcapsules comprising a matrix of substantially water-insoluble shape-retaining alginate gel held together by salt bridges between the carboxyl groups of the alginate.

There are many known prior art methods of encapsulating oleophilic substances. Methods of encapsulating oil-soluble vitamins are disclosed, for example, in U.S. Pat. Nos. 2,183,053; 2,218,591; 2,643,209; 2,650,895; 2,897,119; 3,058,728; 3,099,602; 3,202,731; 3,293,132; 3,608,083; 3,749,799; 3,819,838; and 3,143,475. The vast majority of these and other vitamin encapsulating procedures involve the use of gelatins which are solidified about droplets of vitamin oils by rapidly lowering the temperature and subsequent dehydration.

While methods such as those disclosed in the patent literature set forth above have achieved some significant commercial success, difficulties have sometimes been encountered in rapidly inducing solidification of the encapsulating material. Furthermore, substantial quantities of heat are normally required in the course of gelatin-based processes in order to effectively dissolve the gelatin and to dehydrate the capsules produced.

SUMMARY OF THE INVENTION

The instant invention provides a process for encapsulating oils and oil-soluble substances such as vitamins which overcomes the difficulties of rapid gelation, even in the presence of filler materials, and which requires no large input of heat either to achieve dissolution of the ingredients or to dehydrate the resulting microcapsules. The process accordingly provides a relatively inexpensive method of effectively encapsulating oils and oil-soluble materials such that their resistance to oxidation is improved and their handling is facilitated.

In the process an emulsion is formed which comprises a dispersed oil phase and a continuous phase of an alkali metal alginate and optionally a water-soluble, alcohol-insoluble substance included as an alginate extender or filler. Advantageously, no emulsifying agents need be employed since the alginate effectively serves this function. The emulsion is then formed into discrete droplets and immersed in an alcoholic solution of multivalent cations, typically calcium ions as calcium chloride, to convert the droplets to shape-retaining, substantially water-insoluble alginate gel micro-beads. If a filler is employed, it has been found that despite the presence of the forming alginate gel, it will be precipitated within the alginate matrix. Use of the alcohol based solution in this step, in addition to serving as a precipitation agent for the filler, promotes dehydration of the forming microcapsules. The capsules may then be washed in fresh alcohol to remove salts and promote further drying. Lastly, the capsules are dried to remove residual alcohol.

The microcapsules thus produced comprise a mechanically stable composition of matter which can be handled like a crystalline solid. The capsule wall comprises a matrix of water-insoluble multivalent cation-containing gel and a filler. Within the matrix is a plurality of compartments containing oil droplets shielded from atmospheric exposure.

In preferred embodiments, the filler material is a water-soluble, alcohol-insoluble polysaccharide such as dextran, the alcohol solution comprises a volatile alcohol such as methyl or ethyl alcohol, and the oil is an ingestible nutrient or contains dissolved nutrients such as vitamins A, D, or E.

Accordingly, objects of the invention include the provision of a microencapsulation procedure effective to produce dry granules containing plural discrete droplets of an oleophilic substance completely surrounded by a protective alginate coating. Another object is to provide a stable, substantially dry powder containing a dispersion of fat-soluble vitamins, which powder is substantially insoluble in water but is readily ingested by mammals. Still another object is to provide encapsulation procedures which dispense with the use of gelatins. Another object is to provide a vitamin encapsulation procedure in which rapid gelation of the capsule matrix is effected without subjecting the capsules to a rapid temperature decrease. Yet another object is to provide a microencapsulation procedure wherein solution of the ingredients and drying of the product may be done with improved energy efficiency.

These and other objects and features of the invention be apparent from the following description and from the claims.

DESCRIPTION OF A PREFERRED EMBODIMENT

In the process of the invention, an alkali metal alginate, typically sodium alginate, is dissolved in water at room temperatures to produce a solution containing between about one and four weight percent alginate. This solution is then diluted with a solution of a water-soluble, alcohol-insoluble filler or gel extender consisting of, for example, a 0–30% aqueous solution of a polysaccharide such as dextran. Other suitable filler materials include sodium carboxy methyl cellulose, methyl cellulose, dextrins, and some soluble starches. Preferably, when dextran is used, a 20–30 weight percent solution is prepared. The admixture of equal volumes of dextran and alginate solution results in a mixed solution consisting of between about 0.5 and 2.0 weight percent alginate and 0–15%, preferably 10–15% polysaccharide. Outstanding results have been obtained with between 0.8 and 1.2% sodium alginate and 12% dextran.

Decreased concentrations of alginate in the solution below about 0.5% are increasingly ineffective in producing defect-free microcapsules. Increases of the alginate content above about 2%, while operable, result in a solution having a viscosity which make droplet formation difficult. In general, the concentration of the alginate solution to be used should be increased as the amount of oil to be encapsulated is increased.

Next, the vitamin or other oil to be incorporated into the microcapsules is added to the aqueous solution typically on the order of 1%–10% by weight (optimally 3%–6%). Among the fat-soluble vitamin-active materials useful in the practice of the invention are vitamin bearing oils, pro vitamins and pure or substantially pure vitamins, both natural and synthetic, or chemical derivatives thereof, crude extractions containing such substances, and mixtures thereof. The invention makes possible the preparation of free-flowing powders containing, e.g., vitamin A, vitamin D, and vitamin E active materials as well as vitamin K, carotene and the like, or mixtures of such materials. Preparations of this type are commercially available and typically include pharmaceutically acceptable anti-oxidants of the type well known to those skilled in the art. The amount of oil used may range broadly between about 1.0% and close to 30%. However, at the higher end of the range, the stability of the oil-in-water emulsion is decreased and the quality of the microcapsule is reduced.

The two-phase system is subjected to rapid stirring to induce emulsification of the oil phase in the aqueous phase. Homogenizers, emulsifiers, or other high shear mixing apparatus are useful for this step. Ideally, the resulting emulsion contains oil droplets in the 1–3 micrometer range. Alginate in the continuous phase serves not only as a capsule wall forming material, but also as an emulsifying agent. Accordingly, the emulsion will be found to be pressure stable and easily formed into substantially spherical droplets.

As soon as possible after formation of the emulsion, it is extruded from multiple orifices or otherwise formed into droplets of a size preferably within the range of 300–1,000 micrometers. If desired, the droplet formation can be conducted under an inert gas blanket. The droplets are then immediately collected, while substantially spherical, in a volatile alcoholic, multivalent cation-containing solution, e.g., $CaCl_2$. As the droplets enter the alcoholic solution, calcium ions are exchanged for the alkali metal of the alginate, resulting in the formation of multiple salt bridges between alginate molecules and the creation of shape-retaining calcium alginate beadlets. Any dextran or other alcohol-insoluble polysaccharide is simultaneously precipitated within the alginate framework. This step results in essentially instantaneous gelation of the droplets, at room temperature, and in shrinkage of the droplets caused by dehydration.

Calcium ions, in a concentration of 2.0–2.5 weight percent, are the preferred multivalent cation for this step because of their low cost and low toxicity. Strontium or barium ions may also be used, but magnesium ions will not work. The preferred solvent is a low molecular weight alcohol such as methanol, or ethanol. Such low molecular weight alcohols are preferred because they subsequently can be removed easily from the microcapsule by volatilization. The filler in the microcapsule matrix serves to decrease oil migration within the capsules, reduce material costs and increase wall thickness. The alcohol solution may be regenerated by distillation after use.

As will be apparent from the foregoing, the alcohol solution serves three functions: First, it acts as a carrier for multivalent ions needed to contact and penetrate the liquid droplets in order to convert them from the liquid state to a shape-retaining, substantially water-insoluble gel. Second, where, as preferred, fillers of the type described above are employed, it serves to precipitate the filler within the alginate gel matrix. Third, it promotes dehydration of the microcapsules as water is dissolved in the alcohol.

Microcapsules collected from the solution will be found to contain residual calcium and sodium ions and the anions with which they are associated. These may conveniently be removed by one or more washing steps using salt-free, low molecular weight alcohol. Finally, residual alcohol and moisture is removed by drying the microcapsules, e.g., under vacuum or in air. The product of the foregoing procedure is a substantially dry, free-flowing, solid material comprising multiply compartmentalized microcapsules having little or no tendency to stick together and which contain multiple oil droplets completely encased by the microcapsule matrix. If a filler in the quantities set forth above as the preferred range is employed, the wall thickness of the capsule shields the vitamin or vitamins from making direct physical contact with the surrounding surface.

The invention will be further understood from the following non-limiting examples, wherein all percentages are given by weight.

EXAMPLE 1

100 parts of a 2% sodium alginate (Sigma Chem. Co.) solution is thoroughly mixed at room temperature with 100 parts of a 24% dextran (Sigma Chem. Co.) solution to produce a homogeneous aqueous phase. Five parts vitamin A oil (commercial preparation) is then added to the solution and the two phase mixture is emulsified in a homogenizer (Tekmar) to form an oil-in-water emulsion wherein the oil droplets are generally within the range of 1–3 micrometers. The emulsion is fed through a capillary disposed about one or a few inches above a 2.5% calcium chloride solution in methanol. The spherical emulsion droplets, upon entering the alcoholic solution, immediately gel to form substantially water and alcohol-insoluble micro-beads containing multiple droplets of the vitamin oil. A subsequent wash in methanol and vacuum drying at room temperature yield free-flowing pale yellow spherical micro-beads containing encapsulated vitamin A.

On examination under a microscope, the cross-section of the capsules exhibit a continuous and homogeneous multiply compartmentalized capsule matrix completely enclosing plural oil droplets. Generally, each compartment in separate.

EXAMPLE 2

The process of example 1 is repeated except that 10 parts vitamin oil containing both vitamin A and vitamin D are employed in place of the vitamin A oil of Example 1, the beadlets are dehydrated and washed with isopropyl alcohol and the emulsion contains 10% sodium carboxy cellulose. This procedure results in microcapsules substantially identical to those of Example 1 but having an increased number of encapsulated oil droplets.

EXAMPLE 3

100 parts of the 2% sodium alginate solution of example 1 is admixed with 2 parts vegetable oil. After emulsification, droplets are formed and immersed in a 2.5% $CaCl_2$ solution in methanol. The micro-beads are collected, washed twice in methanol, and vacuum dried. The resulting microcapsules comprise a plurality of vegetable oil droplets encased within a thin film of calcium alginate.

As will be apparent from the foregoing specification, the process of the invention is well suited for producing microcapsules containing essentially any oil or oil-soluble substance including non-food substances. While this description is primarily directed to encapsulation of vitamins intended ultimately as an additive in foods, in view of the foregoing teachings, those skilled in the art will be able to substitute ingredients in place of those specifically disclosed herein when seeking to encapsulate other oils or oil-soluble materials.

Other embodiments are within the following claims.

What is claimed is:

1. A process for producing mechanically stable, multi-compartmentalized capsules containing an oil soluble nutrient, said process comprising the steps of:
   A. forming an emulsion comprising a mixed aqueous solution of an alkali metal alginate and another non-toxic, water-soluble, alcohol-insoluble substance and a dispersed oil phase containing a nutrient;
   B. forming discrete droplets of said emulsion;
   C. immersing said droplets in an alcoholic solution of multivalent cations to convert said droplets to shape-retaining, water-insoluble alginate beads and to precipitate said alcohol-insoluble substance therewithin; and
   D. drying said beads.

2. The process of claim 1 wherein said alcohol-insoluble substance is dextran.

3. The process of claim 1 wherein, between steps C and D, said droplets are washed with alcohol to remove salts.

4. The process of claim 1 wherein said alcoholic solution comprises calcium ions dissolved in methanol.

5. The process of claim 1 wherein said alcoholic solution comprises an alcohol selected from the group consisting of methyl and ethyl alcohol and mixtures thereof.

6. The process of claim 1 wherein said alcohol-insoluble substance is a polysaccharide.

7. The process of claim 1 wherein said nutrient comprises an oil-soluble vitamin.

8. The process of claim 1 wherein said nutrient is selected from the group consisting of vitamin A, vitamin D, vitamin E, and mixtures thereof.

9. The process of claim 1 wherein the alkali metal alginate is sodium alginate.

10. A process for producing mechanically stable, multi-compartmentalized capsules containing at least one oil-soluble vitamin, said process comprising the steps of:
    A. forming an emulsion comprising a continous phase comprising a mixed aqueous solution of sodium alginate and dextran and a dispersed oil phase containing a vitamin;
    B. forming discrete droplets of said emulsion;
    C. immersing said droplets in an alcoholic solution of calcium ions to convert said droplets to shape-retaining alginate beads and to precipitate the dextran therewithin; and
    D. drying the beads.

11. The process of claim 10 wherein, between steps C and D, said droplets are washed with alcohol to remove sodium and calcium ions.

12. The process of claim 10 wherein said alcoholic solution comprises methanol.

13. A process for encapsulating an oleophilic substance within a mechanically stable, multi-compartmentalized substantially water-insoluble matrix, said process comprising the steps of:
    A. forming an emulsion comprising a continuous phase of an aqueous solution of alkali metal alginate, another water-soluble, alcohol-insoluble material comprising a filler and a dispersed oil phase;
    B. forming discrete droplets of said emulsion;
    C. immersing said droplets in an alcoholic solution of multivalent cations to convert said droplets to shape-retaining alginate beads, and to precipitate said filler within the shape-retaining alginate beads; and
    D. drying said beads.

14. The process of claim 13 wherein the alginate is sodium alginate and the alcoholic solution comprises a methanolcalcium chloride solution.

15. The process of claim 13 wherein, between steps C and D, said beads are washed to remove salts.

16. The process of claim 13 wherein said filler comprises a polysaccharide.

17. The process of claim 16 wherein said polysaccharide comprises dextran.

18. A composition of matter comprising a mechanically stable matrix consisting essentially of a water-insoluble multivalent cation containing alginate structure and another water-soluble, alcohol-insoluble polysaccharide, said matrix defining a plurality of compartments containing an oleophilic material.

19. The composition of claim 18 wherein said alginate structure comprises calcium alginate.

20. The composition of claim 18 wherein said polysaccharide comprises dextran.

21. The composition of claim 18 wherein said oleophilic material is a vitamin.

* * * * *